(12) United States Patent
Francavilla

(10) Patent No.: US 8,540,124 B2
(45) Date of Patent: Sep. 24, 2013

(54) DISPENSING PEN

(75) Inventor: Frank Francavilla, Wantage, NJ (US)

(73) Assignee: Lucas Packaging Group, Inc., Branchville, NJ (US)

( * ) Notice: Subject to any disclaimer, the term of this patent is extended or adjusted under 35 U.S.C. 154(b) by 1033 days.

(21) Appl. No.: 11/974,178

(22) Filed: Oct. 11, 2007

(65) Prior Publication Data

US 2009/0095777 A1  Apr. 16, 2009

(51) Int. Cl.
*B67D 7/60* (2010.01)
*B43K 21/00* (2006.01)
*B43K 5/10* (2006.01)

(52) U.S. Cl.
USPC ............. 222/391; 222/386; 401/176; 401/84

(58) Field of Classification Search
USPC .................. 222/391, 386; 401/84, 176–182
See application file for complete search history.

(56) References Cited

U.S. PATENT DOCUMENTS

| | | | | |
|---|---|---|---|---|
| 977,282 A * | 11/1910 | De Vilbiss | | 222/391 |
| 1,718,596 A * | 6/1929 | Smith | | 604/223 |
| 1,823,654 A * | 9/1931 | Hast | | 222/52 |
| 2,090,644 A * | 8/1937 | Seeberger | | 222/323 |
| 2,488,638 A * | 11/1949 | O'Connor | | 401/179 |
| 2,754,033 A * | 7/1956 | Etter | | 222/326 |
| 2,771,858 A * | 11/1956 | Cribbs et al. | | 401/66 |
| 2,776,075 A * | 1/1957 | Etter | | 222/43 |
| 2,778,541 A * | 1/1957 | Sherbondy | | 222/327 |
| 2,784,603 A * | 3/1957 | Collins | | 74/169 |
| 3,076,225 A * | 2/1963 | Sherbondy | | 425/87 |
| 3,378,176 A * | 4/1968 | Snyder | | 222/389 |
| 4,318,499 A * | 3/1982 | Hamilton | | 222/327 |
| 4,323,176 A * | 4/1982 | Sartain | | 222/326 |
| 4,356,938 A * | 11/1982 | Kayser | | 222/327 |
| 4,444,560 A * | 4/1984 | Jacklich | | 222/391 |
| 4,487,341 A * | 12/1984 | Daykin et al. | | 222/391 |
| 4,848,598 A * | 7/1989 | McKinney | | 222/391 |
| 4,886,186 A * | 12/1989 | Andris | | 222/379 |
| 4,892,427 A * | 1/1990 | Ford | | 401/182 |
| 5,433,352 A * | 7/1995 | Ronvig | | 222/391 |
| 5,536,249 A * | 7/1996 | Castellano et al. | | 604/65 |
| 5,593,390 A * | 1/1997 | Castellano et al. | | 604/187 |
| 6,283,660 B1 * | 9/2001 | Furlong et al. | | 401/135 |
| 6,648,181 B2 * | 11/2003 | Whittaker | | 222/391 |
| 6,702,158 B2 * | 3/2004 | Kageyama et al. | | 222/386 |
| 7,241,278 B2 * | 7/2007 | Moller | | 604/211 |
| 7,891,897 B2 * | 2/2011 | Nanos et al. | | 401/112 |
| 2005/0109799 A1 * | 5/2005 | Catani et al. | | 222/391 |

FOREIGN PATENT DOCUMENTS

GB  2211081  *  6/1989 ............ 401/180

* cited by examiner

*Primary Examiner* — Kevin P Shaver
*Assistant Examiner* — Stephanie E Wiliams
(74) *Attorney, Agent, or Firm* — Lerner, David, Littenberg, Krumholz & Mentlik, LLP

(57) ABSTRACT

The present invention is related to a dispensing device. The dispensing device includes a container; a dispensing opening located at one end of the container; a plunger located inside the container; a push button associated with the plunger; and a drive mechanism configured to drive the plunger linearly inside the container from a first position towards the dispensing opening when the push button is pressed and to hold the plunger at a second position, wherein the second position is closer to the dispensing opening than the first position.

11 Claims, 11 Drawing Sheets

DISPENSING PEN

FIELD OF THE INVENTION

The present invention relates to the field of dispensing containers, more particularly to a dispensing pen or a longitudinal dispensing container that is configured to dispense a certain dosage of personal care, pharmaceutical, nutritional, manufacturing fluids or liquids.

BACKGROUND OF THE INVENTION

Dispensing containers that are designed to release personal care, pharmaceutical and nutritional products, for example lotions, are usually made of deformable tubes or bottles that can be squeezed by a user's hand so that the tube releases a dose of the lotion through a dispensing opening. If a user wants a certain dose of lotion, the user simple releases a cap that covers the dispensing opening. Then the user may squeeze the tube to reduce the volume formed by the tube that includes the product that has to be dispensed. The amount of product dispensed corresponds approximately to the reduction of volume of the tube caused by the user's pressure on the tube. The tube or bottle may be made of deformable of plastic or metallic material that can be readily squeezed by a user. A lotion that is contained in the tube will be released by the dispensing opening.

If a precise dosage of the dispensed product is required, a piston syringe can be used for dispensing. The piston may have a transparent body and a scale that is readable by the user. The user can thereby push the piston by a rod from one position of the scale to a next position. Since the scale is made to correspond to dosage units, the user can move the piston with the rod to a position in the scale. Thereby a desired dosage can be dispensed. In the case where the user wants to dispense a dosage without reading the positions of the piston on the scale, complex mechanical assemblies having a linear motors may be used for the dispensing.

Despite all the advancements the designs of dispensing containers, further improvements for dispensing dosages of liquid or semi-liquid products by a dispensing container would be desirable.

SUMMARY OF THE INVENTION

According to a first aspect of the present invention, a dispensing device is provided. The dispensing device preferably includes a container, a dispensing opening located at one end of the container, and a plunger located in the container. The dispensing device further includes a push button associated with the plunger; and a drive mechanism configured to drive said plunger linearly inside said container from a first position towards said dispensing opening when said push button is pressed and to hold said plunger at a second position, wherein said second position is closer to said dispensing opening than said first position.

According to a second aspect of the present invention, a push unit is provided. The push unit can be configured to dispense a product from a container, and preferably includes a housing; a push button located at a rear end of the housing; and a holding unit located at a front end of the housing configured to hold the container. In addition, the push unit preferably includes a push rod that is threadably engaged in a front surface of the housing. The push rod is also configured to push with a front portion against a plunger located inside the container. The push unit may further include a rotator configured to turn the push rod so as to linearly move the front portion away from the front surface of the housing.

According to a third aspect of the present invention, a dispensing device is provided. The dispensing device preferably includes a container, a dispensing opening located at one end of the container; and a plunger located in the container. The dispensing device further includes a push rod configured to press against the plunger, and a push button associated with the push rod. In addition, the dispensing device preferably includes a drive mechanism configured to move the push rod from a first position to a second position when the push button is pressed, and to hold the push rod at the second position. Preferably, the movement of the push rod from the first position to the second position pressed the push rod against the plunger to move the plunger closer to the dispensing opening.

BRIEF DESCRIPTION OF THE DRAWINGS

These and other features, aspects and advantages of the present invention will become better understood with regard to the following description, appended claims and accompanying drawings where:

It should be noted that the dimensions of the assemblies shown in the Figures may be distorted for clarity of illustration, and like numbers represent similar elements.

DETAILED DESCRIPTION

Figure 1:
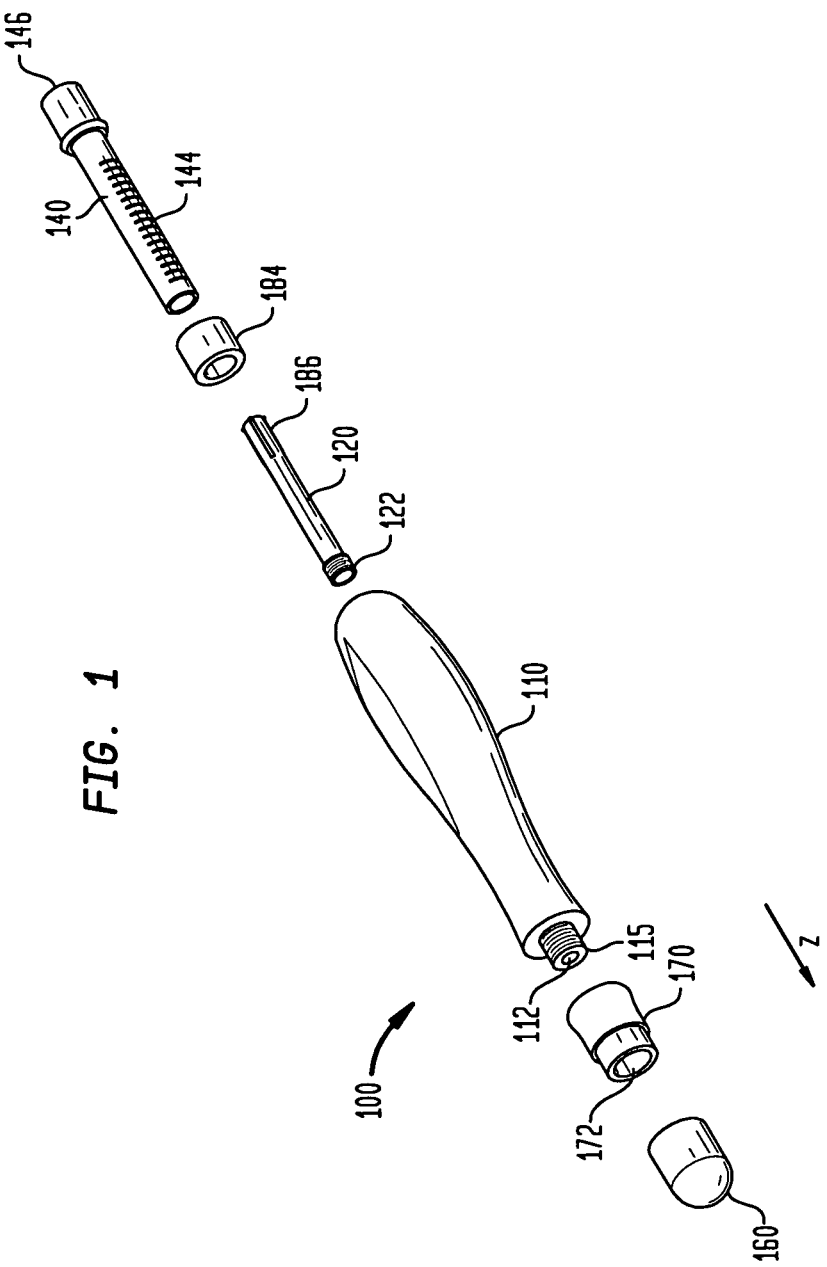
FIG. 1 shows an exploded view of a dispenser pen according to the first embodiment of the present invention.
Figure 2:
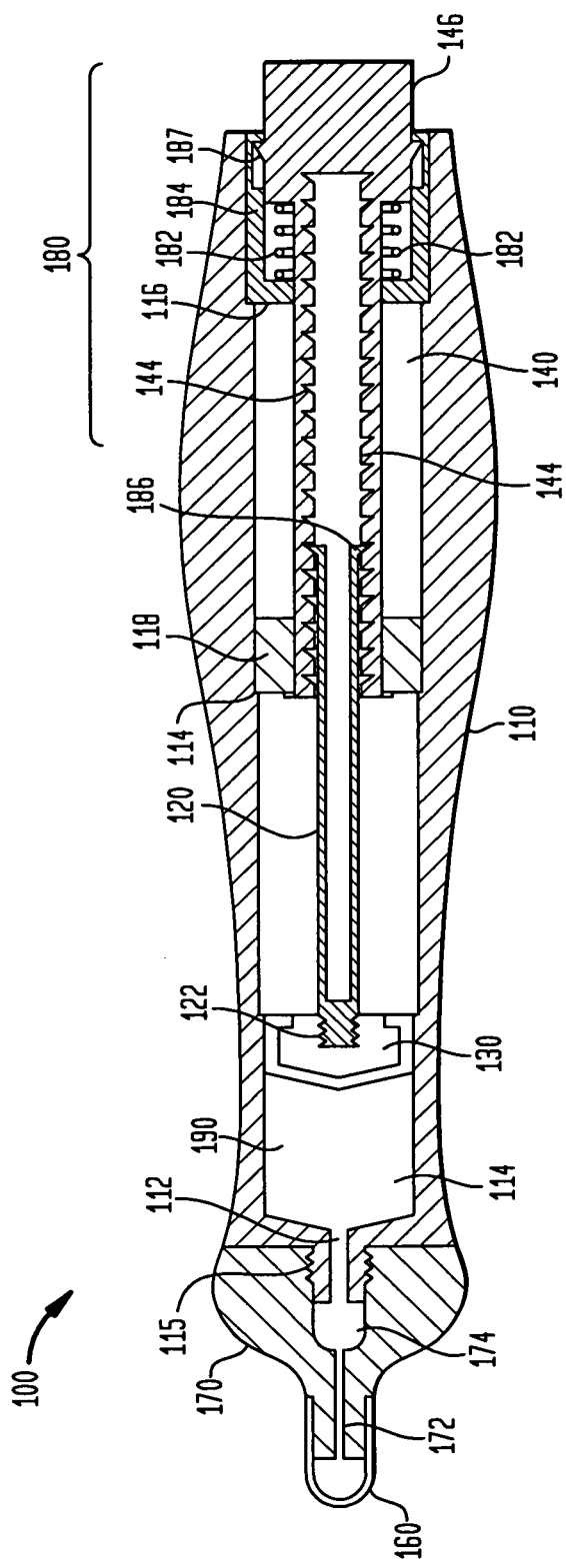
FIG. 2 shows a diagrammatic cross-sectional view of a dispenser pen according to the first embodiment of the present invention.

FIG. 1 shows a perspective exploded view of a dispenser pen 100 according to the first embodiment of the present invention. Pen 100 includes a main body or container 110 that has an interior chamber 114 (FIG. 2). Container 110 can have a shape that can be easily held by the hand of a user. At least one opening 112 is arranged at one end of the container 110. A plunger can be attached or connected to a head 122 of a push rod 120 that are located inside container 110. The plunger 130 can be seen with respect to FIG. 2. The push rod 120 can be moved together with plunger in a step-wise fashion a certain distance in z-direction, once a user presses the push button 146. Push button is arranged on the rear end of longitudinal push jacket 140. Push jacket has a hollow interior space so as to accommodate the push rod 120 when inserted. Rod 120 is configured to move forward out of the jacket 140 each time a user presses button 146. As used in this disclosure, terms such as "front," "forward," "top," "upper," should be understood as referring in direction to the z-axis as indicated in FIGS. 1-12, while the terms such as "back," "backwards," "rear," and "rearwards" should be understood as referring to the negative direction of the z-axis, and need not conform to the normal gravitational frame of reference.

The front portion of the container 110 includes a tip 115 with a thread so that a dispenser head 170 can be screwably attached thereto. The dispenser unit 170 is capable of guiding a product that can be dispensed from opening 112 to dispensing channel 172 of unit 170. The dispensed product will exit by channel 172 from the dispenser pen 100. The dispenser unit 170 can be covered with a cap 160 for protection of the dispensing channel 172 and to avoid leakage of the product that can be dispensed.

The push rod 120 is located and guided inside the push jacket 140 that is itself located inside the container 110. The rear end of the push jacket 140 includes a push button 146 that can be pressed by a user. The push jacket 140 is held with a collar 184 inside the container. The push jacket 140 is suspended with the collar 184 so that a user can pressed button 146 to move push jacket forward in z-direction, and after the user releases the button, the push jacket 140 is pushed back in negative z-direction to its initial position. Push jacket 140 has also engagement slots 144 arranged on the sidewalls along the z-axis that allow engagement with retainer tabs 186 of push rod 120. The tabs 186 and slots 144 are configured to operate as a ratchet to permit forward movement of rod 120 in positive z-direction in a step-wise fashion after a user pressed button 146. The ratchet action also retains the rod 120 at the position on the z-axis if rod 120 is pushed back in negative z-direction.

FIG. 2 is a cross-sectional diagrammatic view of the dispenser pen 100 of FIG. 1 when the components are assembled. Product chamber 114 of container 110 is filled in a front portion with a dispensable product 190, such as a liquid or semi-liquid lotion. Plunger 130 seals the rear end of chamber 114, and can be moved in z-direction to press against product 190. The plunger 130 is attached to a push rod 120 by being threadably engaged with the rear end of the plunger 130 by a thread 122. Push rod 120 is hollow and has rear ends that terminate as retainer tabs 186. The push jacket 140 is also hollow and the hollow opening inside jacket 140 is open towards the front and is wide enough to incorporate push rod 120 therein.

The retainer tabs 186 of push rod 120, slots 144, coil spring 182, stop edges 187 and collar 184 are parts of the drive mechanism 180 that allows advancement of the plunger 130 in z-direction in a step-wise fashion. Coil spring 182 is arranged inside the collar 184, and is configured to push onto an edge of push jacket 140 back in negative z-direction. When a user presses button 146 at the rear end of push jacket 140, spring 182 will contract and push rod 120 will progress in z-direction. Since engagement tabs 186 are located in slots 144 of push jacket 140, the push rod 120 will progress approximately the same distance as the push button 146 is moved in z-direction. When the user releases the push button 146, jacket 140 will be pushed back in negative z-direction by spring 182, while the push rod 120 will be held at the same position by plunger 130. Since the plunger 130 has a frictional resistance with the inner walls of chamber 114, and the sealed space between product 190 and front face of plunger 130 will cause a vacuum effect, the plunger 130 and rod 120 will be prevent plunger from moving back in negative z-direction with the jacket 140.

When jacket 140 is pushed back in negative z-direction, the tabs 186 will exit from the slots 144 and will snap into adjacent slots 144 one position up the z-axis. The tabs 186 are therefore made flexible enough to release from the slot 144 when jacket 140 moves back, and when the plunger is held by friction at the same position on the z-axis. The jacket will be pushed back by spring 182 until stop edges 187 will abut against an edge of a recess in the inner surface of collar 184. A ring 118 located inside container 110 that abuts against edges 114 of the inner walls of container will guide the push jacket laterally. The surfaces of ring 118 that are in contact with jacket 140 provide the lateral guidance and also allows the jacket 140 to slide forward and backwards along the z-axis. Collar 184 is located in the rear portion of container 110, and is abutted against a recessed edge 116 of the inner wall of the container 110. Ring 118 and collar 184 can be attached to the container by a snap and lock mechanism, by threads, or by other attachment means such as glue, etc.

A portion of container 110 is filled with a liquid or semi-liquid product 190 (FIG. 2) that is dispensable through opening 112 and then through channel 172. When the plunger 130 is pushed forward by the user pressing button 146, product 190 is pushed through opening 112 of tip 115 into the dispensing unit 170. It will thereby flow into dosage chamber 174. Dispensing unit 170 has a dispensing channel 172 to dispense the product from dosage chamber 174 by channel 172 to the front end of the dispensing unit 170. Dispensing unit 170 is covered with a cap 160 that can be removed by the user. Unit 170 can also be threadably engaged with tip 115 of container 110 by a thread. For different types of products 190 that can be dispensed, different dispensing units 170 can be mounted to container 110.

Figure 3:
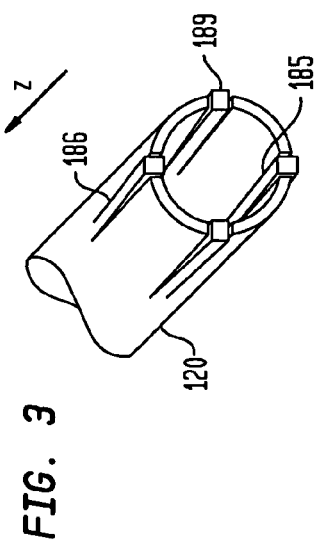
FIG. 3 shows a perspective view of the rear portion of a push rod according to the first embodiment of the present invention.

FIG. 3 shows a perspective view of the rear portion of a push rod 120, showing the engagement tabs 186. The push rod 120 is made of a tubular plastic element that has slots 185 cut in parallel to the z-axis into the rear end of the rod 120. Between slots 185 four engagement tabs 186 are arranged. They correspond to four rows of slots 144 that are arranged in the inner surface of the push jacket 140, so that engagement tabs 186 can operate as pawls in the slots 144 like a linear ratchet. Tabs 186 are thin enough to enable them to bend inwardly when the jacket 140 is pushed backwards by spring 182. Tabs 186 will thereby snap into the next slots 144 of jacket 140. The rear ends of tabs 186 have teeth 189 that protrude radially outwards towards the inner surface of the jacket 140. Tooth 189 has a ramped outer surface that slopes outwardly from the outer surface of push rod 120, to facility disengagement of tooth 189 from the slot 144, when jacket 140 is pushed back.

Figure 4:
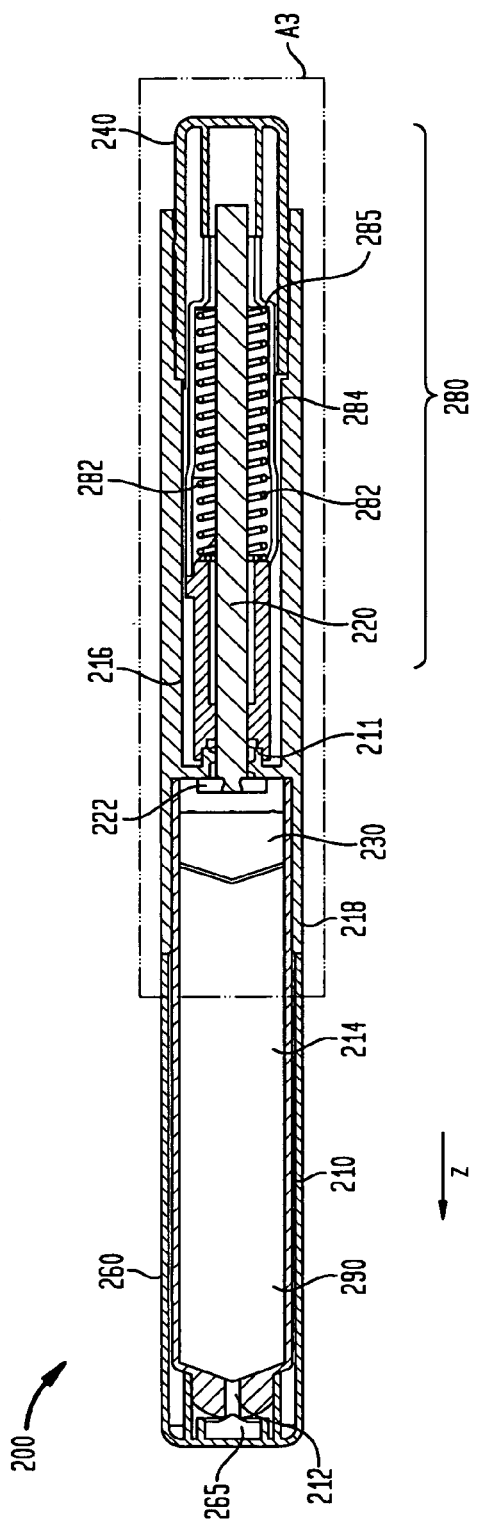
FIG. 4 shows a diagrammatic cross-sectional view of a dispenser pen according to another embodiment of the present invention.

FIG. 4 shows a cross-sectional diagrammatic view of another embodiment of a dispenser pen 200. The dispenser pen 200 includes a removable container 210 and a push unit 216. The container 210 includes a dispensable product 290 filled inside chamber 214 and a plunger 230 that is moveable in z-direction. The plunger 230 forms a seal between the outer walls of the plunger 230 and the inner walls of the chamber 214, so that the product 290 will be sealed inside chamber 214. The container 210 has a dispensing opening 212 at the front end. A cap 260 is placed on container 210 and surrounds a large portion of container 210. Seal 265 is placed inside the cap 260 and is configured to close the opening 212 when the cap is placed onto container 210. The seal is preferably made of a rubber material. The container 210 can be placed onto push unit 216 by inserting it onto holding jacket 218.

The push unit 216 includes a push rod 220 that screwably engages with a front portion 219 of the push unit 216, and the front end of the push rod 220 is connected to an abutment disk 222. Abutment disk 222 is mounted to push rod 220 so as to rotate freely in around the z-axis. Abutment disk 222 is also configured to abut with plunger 230 of the container 210. Drive mechanism 280 is configured to move the plunger 230 step-wise in z-direction each time the push button 240 is pressed by a user. Drive mechanism 280 includes a notched rotator 286, a spring 282 and a rotative engager 284. The rotator 286 can turn clock-wise around the z-axis and is abutted against front portion 219. The engager 284 can turn clockwise around the z-axis by a certain angle, when a user presses the push button 240. Spring 282 is partially surrounded by engager 284, and suspends engager 284 with a rear face of notched rotator 286.

Figure 5:
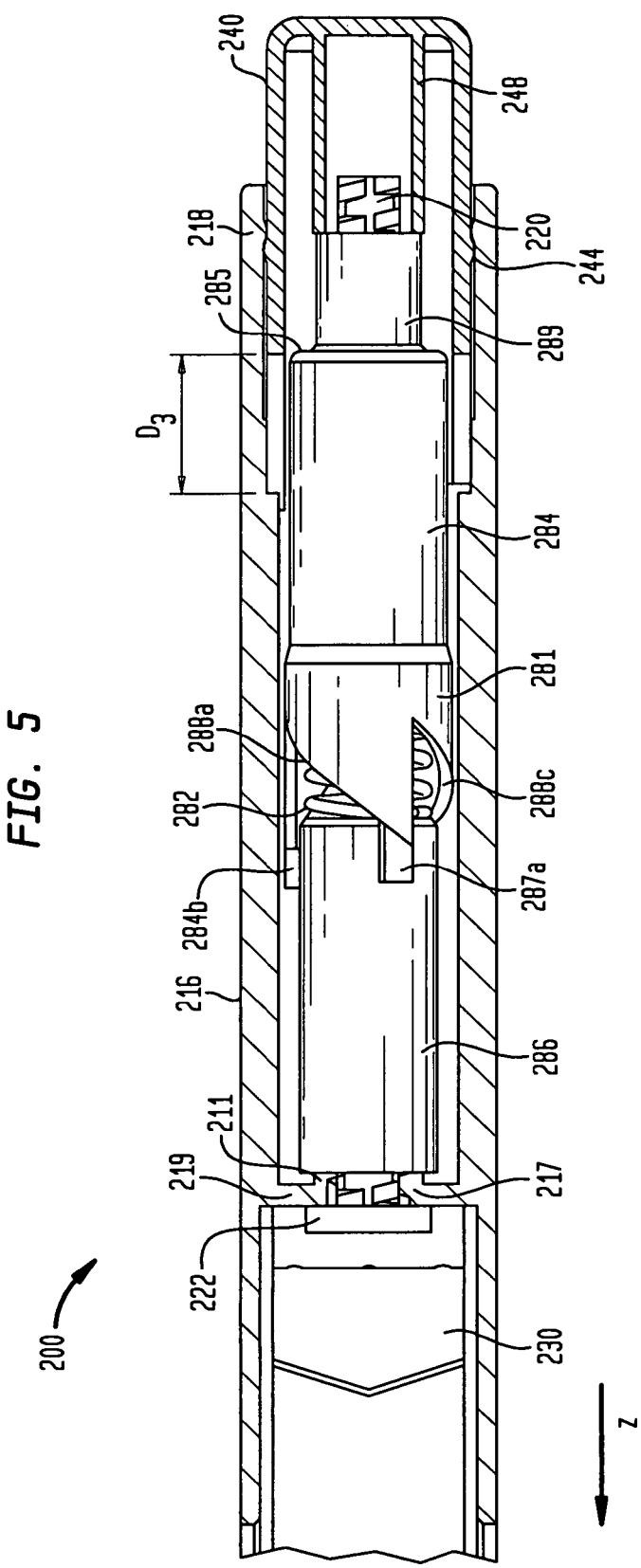
FIG. 5 shows a partial cross-sectional and assembled view of a dispenser pen according to another embodiment of the present invention.

FIG. 5 shows a partial cross-sectional and assembled view of the area A3 shown in FIG. 4. At least a portion of push rod 220 is threaded. The thread of push rod 220 corresponds to a thread of the opening 217 of the front portion 219. Push rod 220 can thereby threadably engage into front portion 219 and be turned clockwise to progress in z-direction. Thereby push rod 220 will linearly move abutment disk 222 in z-direction. A rotation of push rod 220 by a certain angle will correspond to a linear movement of abutment disk 222. The notched rotator 286 is configured to engage with push rod 220 so as to rotate with rod 220, while a movement of rod 220 in z-direction is not obstructed. On an outer cylindrical surface of rotator 286, three notches 287a, 287b and 287c are arranged, having a slanted rear surface that can abut with saw-tooth like front surfaces 288a, 288b, and 288c of crown 281. Crown 281 is a front portion of rotative engager 284. The inner diameter of crown 281 is bigger than the outer diameter of the body of notched rotator 286 in a radial direction, so that crown 281 can partially encircle the rear end of the notched rotator 286. Spring 282 is engaged between the rear face of the rotator 286 and an abutment edge 285 of the engager 284. Push button 240 can be pressed to move engager 284 in z-direction by distance D3 by contracting spring 282. For this purpose, the front surfaces of the jacket 248 of button 240 abuts against the rear surface of thrust cylinder 289 of engager 284.

Figure 6:
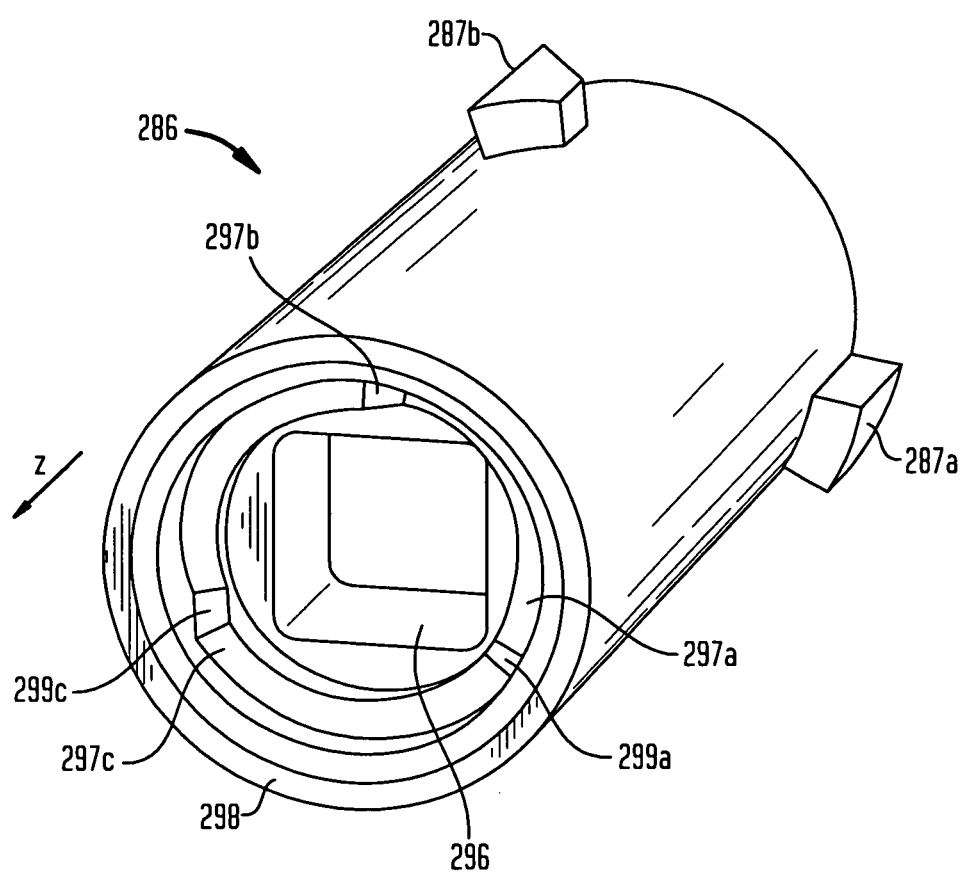
FIG. 6 shows a perspective view of a notched rotator used in another embodiment of the present invention.

FIG. 6 shows a detailed perspective view of an exemplary notch rotator 286. The rotative engagement of the rotator 286 with push rod 220 is performed by nut 296 that embraces the push rod and has a square cross-sectional opening. The threaded push rod 220 has also a square cross-sectional shape if cut perpendicular to the z-axis, and push rod 220 that can be inserted through nut 296. Therefore, push rod 220 can freely move in z-direction, but is rotatably engaged with the rotator 286 by the square opening of nut 296. The front portion of rotator 286 also has a recessed edge with ramped surfaces 297a, 297b, and 297c and steep surfaces 299a, 299b and 299c, circularly arranged to form sections of a front surface of a ring.

Figure 7:
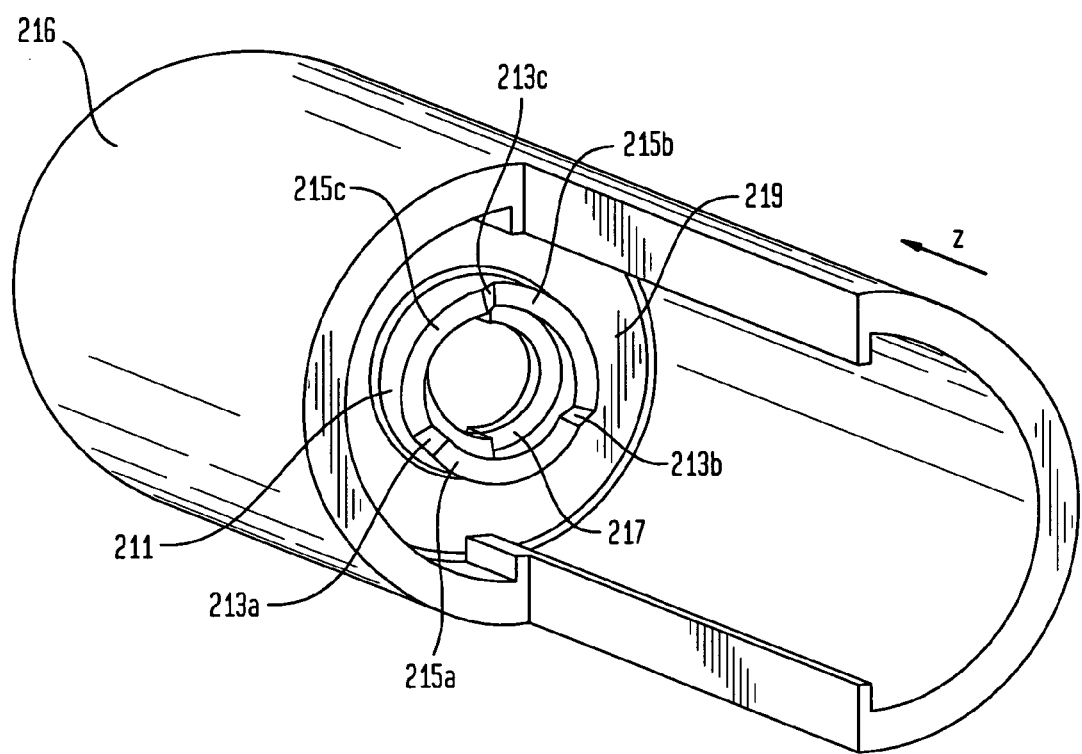
FIG. 7 shows a partial cross-sectional perspective view of a portion of a push unit used in another embodiment of the present invention.

FIG. 7 shows a detailed partial cross-sectional view of the push unit 216 with a front portion 219 that complements mechanically to the notch rotator 286 shown in FIG. 6. A protruding ring 211 is arranged in the center of the front portion 219 of push unit 216, and encircles opening 217. Opening 217 has a thread corresponding to the thread of push rod 220. The rear surface of protruding ring 211 has ramped surfaces 215a, 215b and 215c, and steep surfaces 213a, 213b, and 213c, that together from multiple sections of the rear surface. The front portion of rotator 286 complements with the rear surface of protruding ring 211.

If a user presses button 240 in z-direction by a distance D3, spring 282 will compact. Engager 284 will move by distance D3 in z-direction. Surfaces 288a, 288b and 288c of crown 281 will slide against the slanted rear surfaces of notches 287a, 287b, 287c. The notches 287a, 287b and 287c will move into the lower corners of the teeth of crown 281. The sliding of notches 287a, 287b, and 287c against the teeth of crown 281 will turn rotator 286 with reference to engager 284 by approximately a third of a full rotation, being 120°. Since push rod 220 will be turned together with rotator 286, push rod 220 will also turn approximately 120°. In consequence, rod 220 will turn inside the thread of opening 217, and abutment disk 222 will displace by a dosage distance in z-direction to a new position.

When a user releases the button 240, the button will be pushed back by extracting spring 282, and engager 284 will be pushed back to the initial position so that stop barrier 244 of button 240 can engage with stop barrier 218 of the push unit 216. Notches 287a, 287b, and 287c will slide back to the initial position close to the upper edges of the teeth of crown 281. The front face of rotator 286 will be pushed against opening 217. Engager 284 will have rotated approximately 120° during the pressing of button 240. If the user presses and releases button 240 again, the push rod 220 will further progress a dosage distance in z-direction.

When a removable container 210 is placed on push unit 216, the abutment disk 222 will abut against plunger 230 of the removable container 210. Plunger 230 will also advance by a dosage distance in z-direction. This will reduce the volume of main chamber 214, so that product 290 will be dispersed by opening 212, when the cap 260 is removed from the dispenser pen 200. The user can repeatedly press button 240 until plunger 230 arrives at the front end of main chamber 214, and little or none of the product 290 is remaining in chamber 214. Since the distance D3 of the push button 240 in z-direction can be bigger than the distance traveled by abutment disk 222 through the translation of the movement in a rotation by rotator 286 and engager 284, as well as the chosen thread ratio of opening 217, the force that will act in z-direction by abutment disk can be increased comparing with the force applied when pushing button 240. Depending on many factures such as viscosity of product 290, diameter of opening 212, different pressure ratios may be realized by the mechanical design of dispensing pen 200.

To prevent rotation of rotator in counter-clockwise direction seen along the z-axis, rotator 286 is inserted into push unit 216 and is abutted against front portion 219 with pressure exerted by spring 282 (FIG. 5). The front part of rotator 286 thereby encircles at least a portion of protruding ring 211. When the rotator 286 is turned clock-wise inside the push unit 216 by the movement of engager 284 in z-direction, the ramped surfaces 297a, 297b and 297c of rotator 286 will slide clock-wise against counterpart ramped surfaces 215a, 215b, and 215c on the protruding ring 211 (FIG. 7). Since the circumference of the front surface of ring 211 is separated in three sections defined by the ramped surfaces 215a, 215b, and 215c, after the rotator 286 has turned approximately 120°, the ramped surfaces 297a, 297b and 297c will slip over steep surfaces 213a, 213b, and 213c, and slip over to the adjacent steep surface 213b, 213c, and 213a. At this point, the steeps surfaces 299a, 299b, and 299c will be engaged with a corresponding step surface 213a, 213b, and 213c, and this engagement prevents any counter-clockwise back rotation.

The arrangement of notches 287a, 287b and 287c on the outer surface of rotator 286 are located at circumferential positions close to the locations of step surfaces 299a, 299b, and 299c, so that the movement of the engager 286 towards the rotator will allow a relative rotation between engager 286 and rotator 284 of approximately 120°. The ramped surfaces 297a, 297b, and 297c will snap into a next position of the protruding ring 211, with corresponding steep surface abutting against each other. This arrangement will favor clockwise movements, and will prevent counter-clockwise turns.

In the variant shown, engager includes three notches 287a, 287b, and 287c, that will turn the rotator 286 by approximately 120°. However, a different number of notches are also possible. For example, there can be four notches, where the rotation step is 90°, or seven notches, where the rotational step would be 360°/7. The container 210 that is placed onto push unit need not to have a cylindrical shape, many other container shapes are possible that can be engaged with a push unit 216 by a corresponding holding jacket 218.

Figure 8:
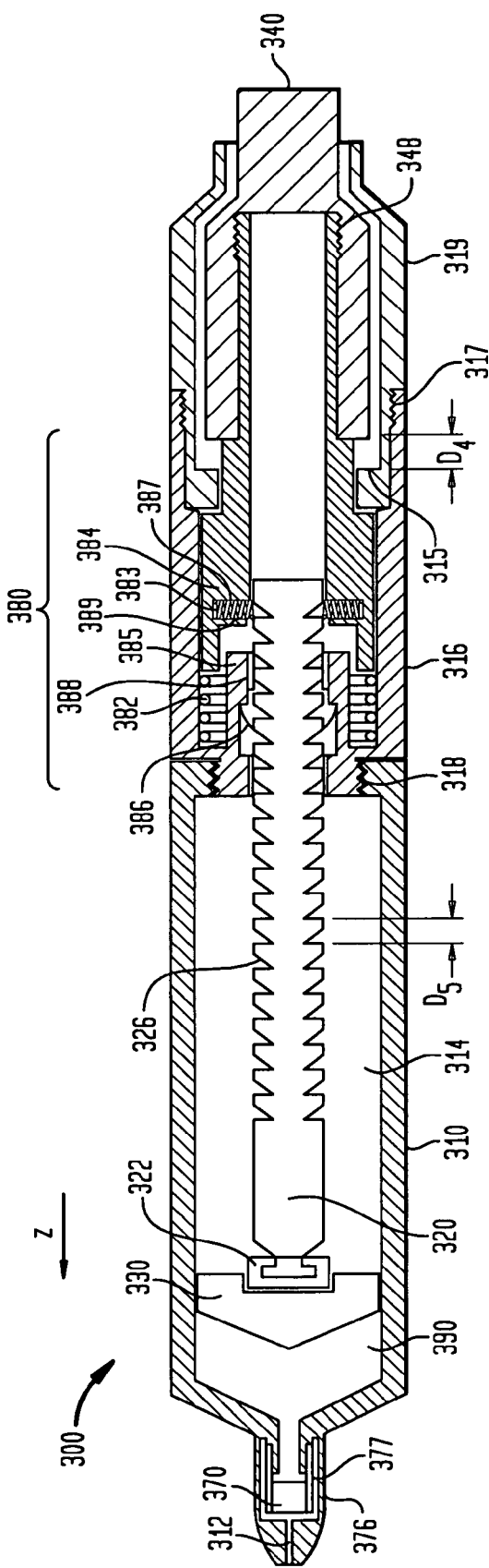
FIG. 8 shows a diagrammatic cross-sectional view of a dispenser pen according to yet another embodiment of the present invention.

FIG. 8 shows a cross-sectional diagrammatic view of yet another embodiment of a dispensing pen 300. Pen 300 includes a removable container 310 and a push unit 316. The container 310 includes a dispensable product 390 in a chamber 314 and a plunger 330 moveable in z-direction. The plunger 330 forms a seal between the outer walls of the plunger 330 and the inner walls of the chamber 314. Container 310 has a dispenser opening 312 at the front end. The container 310 can be screwably engaged onto push unit 316 by thread 318. The front tip 370 includes radial holes 377, and the front tip is circumferentially covered with a cylindrical jacket 376. Cylindrical jacket 376 is made of an elastically stretchable material so that it forms a valve-like membrane over the radial holes 377. When plunger 330 pushes product 390 in z-direction, pressure will be exerted onto the jacket 376 so that it will expand radially and allow product 390 pass through radial holes 377 and exit by opening 312.

The push unit 316 of pen 300 includes a drive mechanism 380 configured to move the push rod 320 in a step-wise fashion each time a user pressed button 340. Push rod 320 has therefore ratchet grooves 326 on an outer surface with a pitch D5. Pitch D5 is configured to set a required dispensing dosage per pitch. Drive mechanism 380 includes a retainer spring 386, counter spring 382, engaging element 384, and holding jacket. The engaging element 384 includes a ratchet pawl 387, stop spring 383, and an abutment disk 389. At the rear end of engaging element 384, a push button 340 is screwably mounted to the engagement element by thread 348. A portion of push button 340 exits the rear casing 319 of push unit 316. Rear casing 319 is also screwably attached to the push unit 316 by a thread 317. Push rod 320 is guided inside the push unit by slider elements 388.

Push button 340 is shown in an initial position before being pressed by a user (FIG. 8). A user can press push button 340 in z-direction to move it by a distance D4, until the front end of the button 340 abuts against stopper ring 315 or abutment disk 389 abuts against the rear face of holding jacket 385. The movement is countered by counter spring 382 that is pushing against the front face of engaging element 384 in negative z-direction. Therefore, after the user releases button 340, engaging element 384 and button 340 will move back to the initial position. During the pressing, push rod 320 will advance by a ratchet groove pitch D5, and retainer spring 386 located inside the holding jacket 285 will snap into the next ratchet groove 326 in negative z-direction. To ensure that the retainer spring will engage into the next ratchet groove, distance D4 must be at least as long as distance D5 of the pitch.

Preferably, distance D4 is slightly longer than D5, so that retainer spring can easily snap over to the next tooth.

The snapping of spring 386 into the adjacent groove can be heard by the user, and this audible feedback will provide a signal to the user to release press button 340. With push rod 320 held by spring 386 at the new position, engaging element 320 will be pushed pack back spring 382 until it abuts against ring 315. The ratchet pawls 387 will exit from the ratchet groove 326 and move to the adjacent ratchet groove 326 in the negative z-direction. Spring 383 will push ratchet pawl 387 back into the next ratchet groove 326.

Dispenser pen 300 is a modular design with elements that are screwably interconnected with each other. For example, rear casing 319 can be screwed onto push unit 316. This allows easy assembly and disassembly for maintenance, repositioning of the push rod 320 and abutment disk 322 to the initial position for reuse, etc. In this design, push rod 320 can be pulled out of push unit 316 in z-direction, and can be reinserted into push unit 316, before button 340 and rear casing 319 are screwably fasteded to push unit. For this purpose, abutment disk 322 can be removed from push rod 320 and can be clipped back onto the push rod 320 once it is reinserted into unit 326. In another variant, ratchet pawls 387 and spring 383 are replaced by a spring that has the same or similar design as spring 386, thereby simplifying the design of pen 300. Different types of containers 310 can be placed onto push unit, for different applications and types of dispensing of products.

Figure 9:
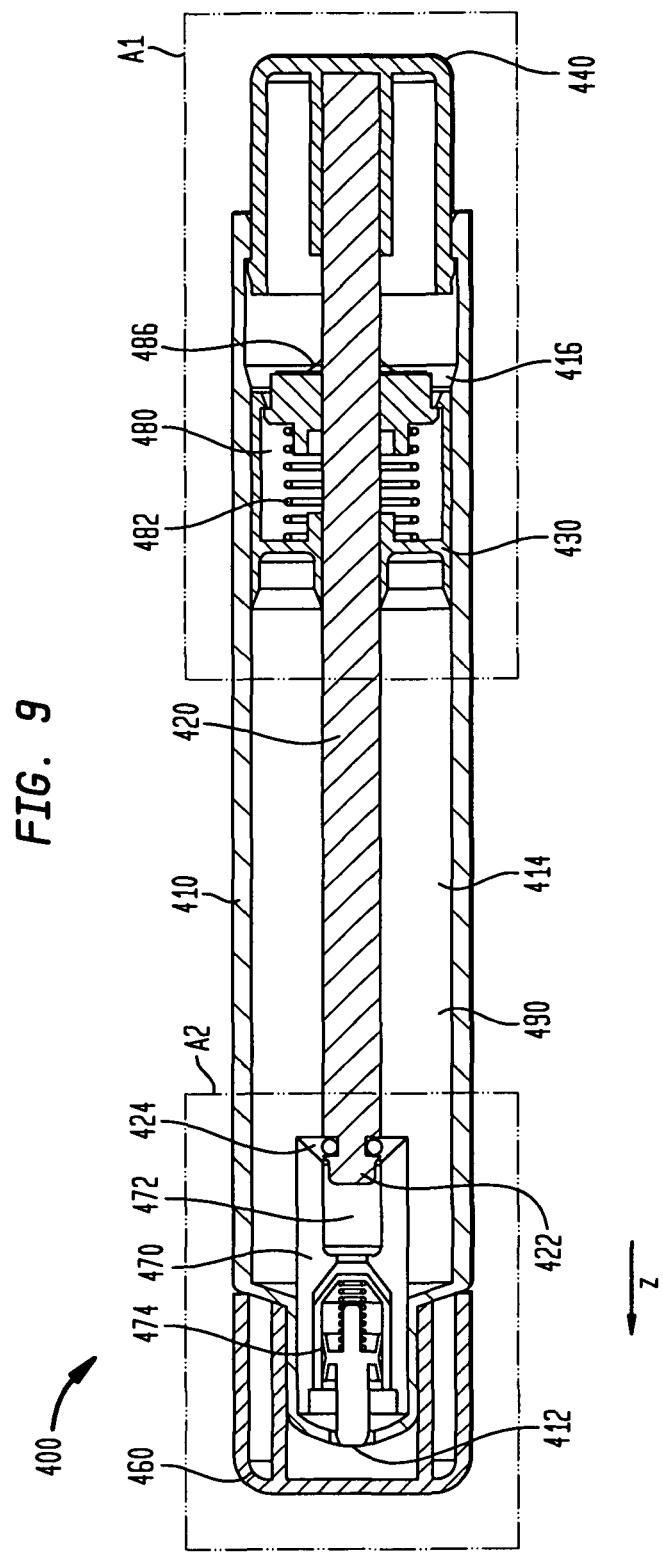
FIG. 9 shows a diagrammatic cross-sectional view of a dispenser pen according to the still another embodiment of the present invention.

FIG. 9 shows a diagrammatic cross-sectional view of a dispenser pen 400 according to still another embodiment of the present invention. Pen 400 includes a container 410 that may have a cylindrical form, having an opening 412 at one end of the container 410. At least a portion of container 410 is filled with a liquid or semi-liquid product 490 that is dispensable through opening 412. A plunger 430 is located inside container 410 and forms a seal to prevent product 490 from escaping. The plunger 430 can also be moved in z-direction if a user presses the push button 440 arranged on the other end of container 410. Plunger 430 is shown in a position before any of the product 490 has been dispensed, and is abutting against a front face of seal disk 416. The push button 440 is connected to a rear end of push rod 420. Rod 420 traverses seal disk 416 and plunger 430 substantially in the center. Every time a user presses push button 440, the volume of main chamber 414 including the product 490 is reduced, since the plunger 430 will be moved forward by the push rod 420 to advance to a new position in direction of the z-axis.

A drive mechanism 480 is arranged partially surrounded by the plunger 430 and surrounding push rod 420. Drive mechanism 480 is moveable relative to the push rod 420 and the plunger 430. The mechanism 480 includes a retaining lever 487 (FIG. 10) that will engage in the surface of push rod 420 when a user presses the push button 440. When push rod 420 is pushed in negative z-direction, lever 487 will disengage from the surface of push rod 420. Levers 487 will slip on the surface of rod 420, and disk 484 can slip relative to push rod. Plunger 430 is mechanically suspended to the mechanism 480 by coil spring 482.

The cylindrical container 410 further includes a valve unit 470. When a user presses button 440, valve unit 470 is configured to guide product 490 from the main chamber 414 towards the opening 412 of cylindrical container 410 for dispensing the product. When a user does not press button 440, valve unit is configured to close the container 410 to thereby prevent product 490 escaping from container 410. For dispensing a certain amount of a product, valve unit 470 includes a dosage chamber 472. Before a user presses the push button 440, dosage chamber 472 is filled with product 490. A front tip 422 of the push rod 420 is configured to protrude into dosage chamber 472, when a user presses the push button 440. By using seal 424 that surrounds push rod 420, the ingression of top 422 into the dosage chamber 472 will compress product 490 inside chamber 472. The product can escape through valve 474 out towards opening 412. During this piston-like action of tip 422 and chamber 472, dosage chamber 472 is sealed towards main chamber 414. None of product 490 can flow from the main chamber 414 towards dosage chamber 472 or opening 412.

Figure 10:
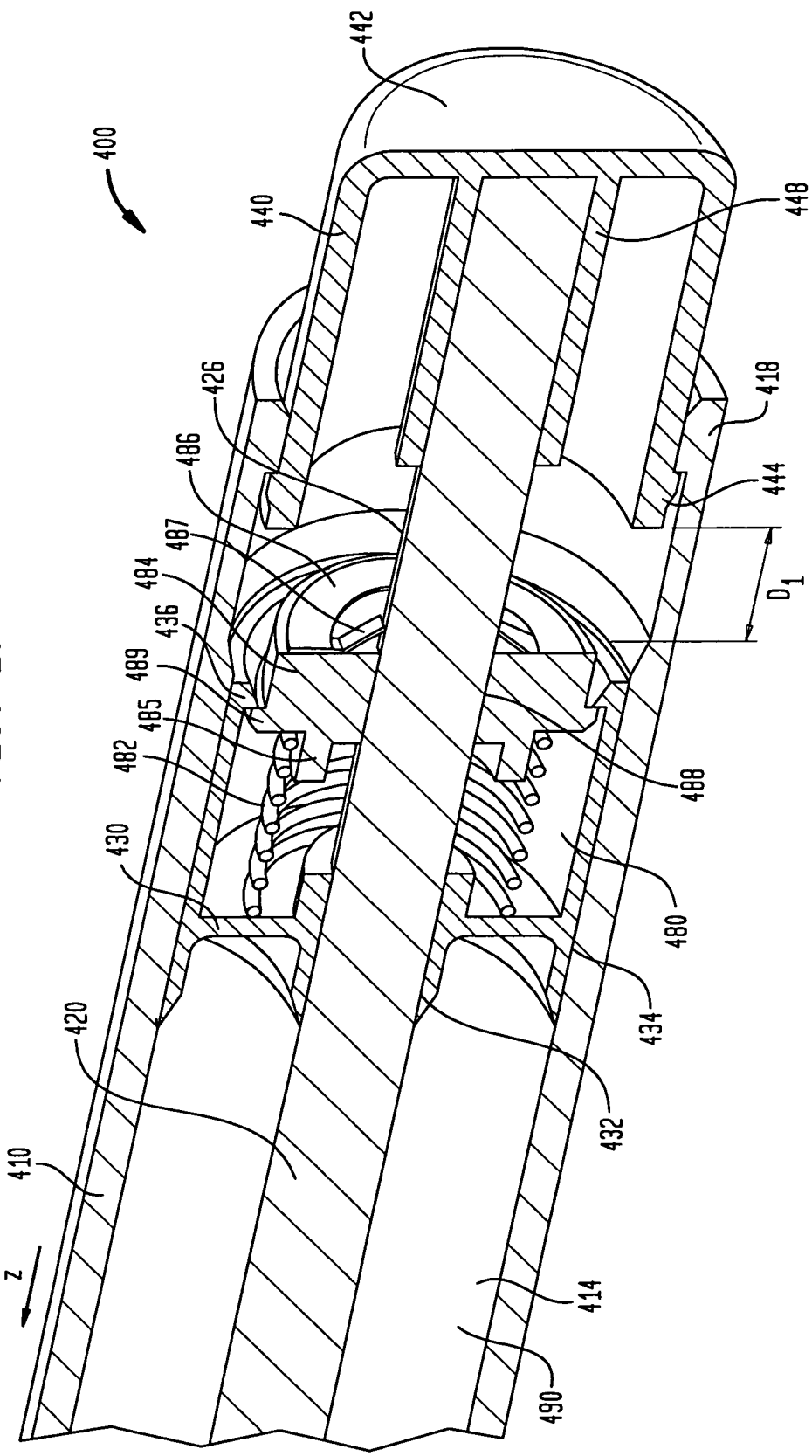
FIG. 10 shows a diagrammatic cross-sectional perspective close-up view of area A1 shown in FIG. 9 according to the still another embodiment of the present invention.

FIG. 10 represents a cross-sectional diagrammatic perspective close-up view of the area A1 of FIG. 9, depicting the rear end of the dispenser pen 400 with the push button 440. The plunger 430 is shown in its initial position before any of product 490 is dispensed. For representation purposes, seal disk 416 has been removed to better show elements of mechanism 480. Push button 440 includes a rear pressing surface 442, a push rod holding jacket 448, and stop barrier 444 arranged around the inner circumference of the push button 440. An edge of stop barrier 444 can engage with a corresponding stop barrier 418 at the rear end of container 410, when button 440 is pressed by spring 482. When a user presses button 440, button 440 can move forward by distance D1. After the user releases button 440, button 440 will move back to abut against stop barrier 418. Plunger 430 can slide along the z-axis and having a sliding surface 434 with the inner wall of the cylindrical container, and sliding surface 432 with push rod 420. Plunger 430 also includes a stop ring 436 that is arranged around the circumference of the rear end of the plunger 430. The sliding surfaces 432, 434 are made such that they form a seal to retain product 490 in the main chamber 414 without leakage between the plunger 430 and the container 410, or the push rod 420, respectively.

Mechanism 480 includes a spring 482, a pressure disk 484, collar 485, ring 486 connected to retaining levers 487, and a stop ring 489. The retaining levers 487 are configured to allow slipping of the pressure disk 484 in positive z-direction, since the levers 487 can glide along the surface 426 of push rod 420. However, when the pressure disk 484 is pushed back to along the negative direction of the z-axis, for example by pressure exerted with spring 482, the levers 487 will engage with surface 426 and will block pressure disk 484 from sliding back in negative z-direction. Coil spring 482 can push plunger 430 forward until rear surface of stop ring 489 of the pressure disk 484 engages with the front surface of stop wall 436 of plunger 430. Every time plunger 430 is moved forward, the volume of main chamber 414 is reduced. Collar 485 is configured to have an outer diameter that corresponds to an inner diameter of spring 482, so that coil spring 482 can be mounted to the pressure disk 484. Surface 488 between push rod 420 and pressure disk 434 allows pressure disk 434 to slide in z-direction along rod 420, if not prevented by levers 487.

Figure 11:
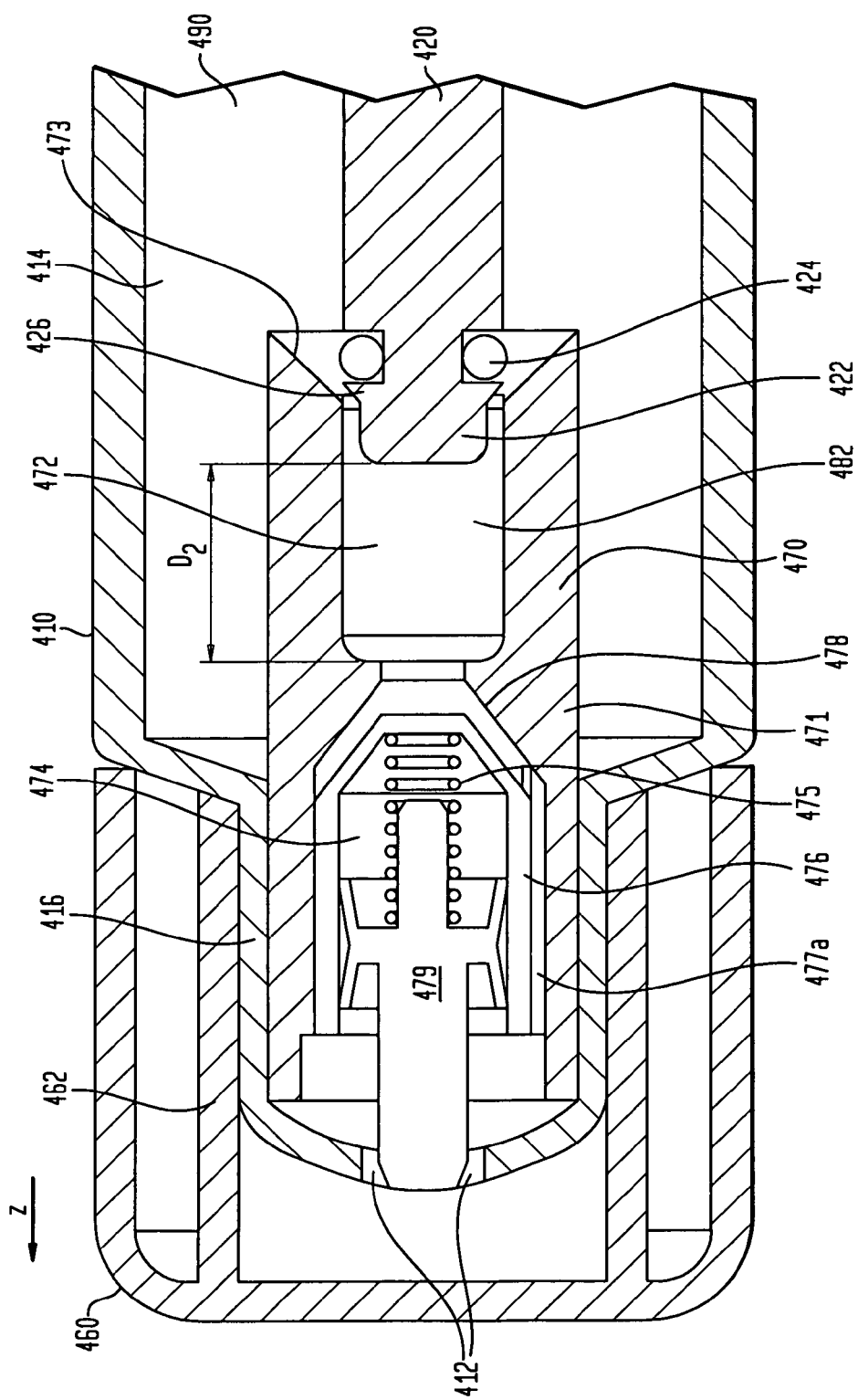
FIG. 11 shows a diagrammatic cross-sectional close-up view of area A2 shown in FIG. 10 according to still another embodiment of the present invention.
Figure 12:
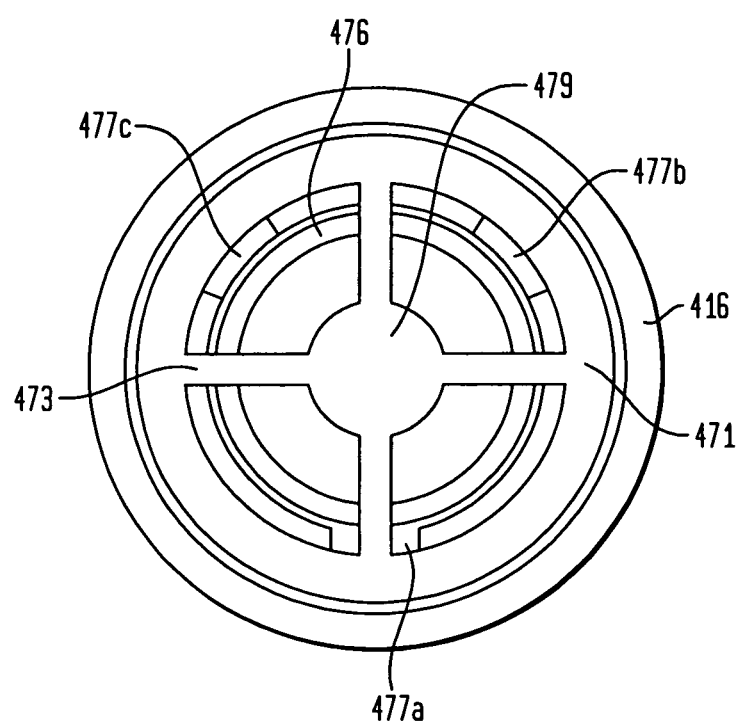
FIG. 12 shows a diagrammatic cross-sectional view along line C of FIG. 11 according to the first embodiment of the present invention.

FIG. 11 represents a cross-sectional diagrammatic close-up view of the area A2 of FIG. 9, depicting the front end of dispenser pen 400 with valve unit 470. The dispenser pen 400 has a front tip 416 having a reduced diameter comparing with container 410. A cap 460 having an inner jacket 462 is placed onto the front tip 416. The jacket 462 has an inner diameter that is slightly bigger than an outer diameter of the wall forming the front tip 416, so that the cap 460 can be manually put on and removed from front tip 416. A valve unit 470 is attached to the inner side of the wall forming tip 416. In the variant shown, the valve unit 470 is a cylindrical element configured to dispense a certain dosage of liquid 490 in container 414 through opening 412. The valve unit 470 includes a dosage chamber 472 with beveled front edges 473 and a valve 474. Valve 474 includes a movable valve cap 476 and an inner holder 479 that is mechanically secured with the cylinder 471 of the valve unit 470 with radial links 472 (FIG. 12). The valve cap 476 is movable for a limited distance in z-direction in relation to cylinder 471 and inner holder 479. A spring 475 suspends valve cap 476 with the inner holder 479, and presses valve cap in a closed position onto conical outlet 478.

FIG. 12 shows a cross-sectional view of the tip 416 along the line C shown in FIG. 11. The tip 416 is formed by a cylindrical element that surrounds the cylinder 471 of valve unit 470. Cylinder 471 is mechanically connected with four radial links 473 to the inner holder 479. Between the movable valve cap 476 and the cylinder 471, three dispensing channels 477a, 477b, and 477c are arranged. A product 490 will be dispensed through these channels to exit by opening 412.

While the pressure disk 484 may be made of a plastic material, the spring 482, ring 486 and levers 487 may be made of metal, for example a stainless steel. It is also possible that the surface 426 has ratcheting teeth, marks or grooves, so that the retaining lever 487 will engage in a groove to better hold pressure disk 484 at a position along the z-axis. In the case where the surface 426 of rod 420 has no ratcheting teeth, surface 426 may be made of a soft plastic material that allows easy engagement of retaining levers 487. In the variant shown in FIG. 10, the dispenser pen 400 has a container 410 having a cylindrical shape. The cross-sectional shape of the dispenser pen 400 cut perpendicularly to the z-axis is therefore round. However, other shapes are also possible, such as oval, rectangular shapes with round edges, flat bars with rounded ends, etc. are also possible.

Next, the dispensing of a product 490 located in container 410 is described. First, a user presses push button 440 (FIGS. 9 and 10) by distance D1, push rod 420 will move forward and the front tip 422 will ingress into dosing chamber 472. At ingression, rod 420 will be radially centered by the beveled edges 473 of the rear ends of cylinder 471 and the conical edges 426 of the front tip 422. Seal ring 424 will come into contact with inner walls of chamber 472 and form a seal that allows the push rod 420 to press out product 492 located in chamber 472 in z-direction in a piston-like action. The distance D2 traveled by tip 422 corresponds to distance D1 of the push button (FIG. 10).

The pressure exerted on the product 492 by the tip 422 of push rod 420 will increase pressure in the dosing chamber 472. This pressure will push valve cap 476 to the front. Valve cap 476 will therefore move from a closed position abutting against a conical outlet 478 to an open position, and will thereby open channels 477a, 477b and 477c (FIG. 12). The product 492 located inside chamber 472 will be pressed past the conical outlet 478 and will move through channels 477a, 477b, and 477c. Product 492 can then exit and is dispensed through openings 422.

While the user has pressed button 440 to advance rod 420 by distance D1, pressure disk 484 will have compacted spring 482 by progressing in z-direction by approximately a same distance D1, since retaining levers are engaged in push rod 420. Plunger 430 however will also move forward on the z-axis. That is, there is sufficient interference between push rod 420 and retaining levers 487 that plunger 430 can advance forward, while at the same time spring 482 causes push rod 420 to retract back out of chamber 472. Thus, the forward motion of push rod 420 expels the product 490 out of chamber 472, and the spring 482 continues to apply pressure to refill chamber 472 for the next dosage to be applied therefrom. By the compacted spring 482, plunger 430 will exert pressure on chamber 414, since none of product 490 in main chamber 414 can enter into chamber 472.

Second, when the push button 440 is released, by spring 482 pushing against plunger 430 and pressure disk 484 (FIGS. 9 and 10), push rod 420 will be retracted out of chamber 492 in negative z-direction. Push rod 420 can slip against disk 484 by disengagement of levers 487. A filling gap for dosage chamber 472 will be formed between the seal ring 424 and the edges 473, as soon as tip 422 exits chamber 472. Product 490 from main chamber 414 can flow into dosage chamber 472. Since most of product 492 in dosage chamber 472 will have exited by the channels 477a, 477b, 477c, valve unit 470 will close since valve cap 476 will move back to a closed position to abut on conical outlet 478.

Third, plunger 430 is pushed in z-direction with spring 482. The pressure exerted on product 490 in z-direction can refill chamber 472 with a new dose of the product 490. The volume of dosage chamber 472 that will be traversed by tip 422 with distance D2 defines the dispensed dosage, and can be designed for different dosages. The pressing of button 440 by user can be repeated until plunger 430 will abut against valve unit 470. The user can repeat pressing button 440, until cap 440 abuts against front portion of container 414, and all or most of product 490 is dispensed.

Other types of valve units are also possible. For example valve unit may be used, having brushes, blending tips, pads, etc. depending on the required application for the dispenser pen 400. Spring 475 can be made of different spring forces depending on the application and dispensed product. For the description of the first embodiment of dispenser pen 400, valve unit 470, etc., the description refers to circular-symmetric elements such as "cylinder," or "ring." However, the form and shape of these elements need not be circular. Other volumetric forms for valve unit 470, container 410, plunger 430, push button 440 are also possible, for example rectangular shapes with rounded corners, oval shapes, etc.

The elements of the dispenser pens 100, 200, 300, and 400 can be made from various materials. As an example, the components may be made of polypropylene plastic components. Any surface that is slidable can be coated to provide low friction. An interface between plunger and container may be coated as to provide appropriate sealing of chambers containing the product. The springs may be made of metal, for example stainless steel or leaf spring metal that is covered with a plastic film to prevent corrosion.

The invention as described herein includes many elements having mechanical functions such as exerting pressure, rotative engagement, sealing, etc. Mechanical components having functional equivalents of the above described mechanical components are also within the scope of the invention. For example, retainer spring 387 can be made of plastic levers, pivotable ratchet pawls, stiff brushes, etc. having the same function of avoiding the push rod 320 regressing in negative z-direction. As another example, valve unit 470 can be made my other functional equivalent valve systems that prevent product 490 flowing out of container 410, when the user does not press button 440.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A dispensing device, comprising:
a container;
a dispensing opening located at one end of said container;
a plunger located in said container;
a push button associated with said plunger, said push button having a stop edge; and
a drive mechanism configured to drive said plunger linearly inside said container from a first position towards said dispensing opening when said push button is pressed and to hold said plunger at a second position, the drive mechanism including
  a push rod in contact with said plunger for moving said plunger linearly inside the container, said push rod being aligned with the push button and including at least one ratcheting tooth;
  an elastic element positioned around said push rod;
  a retaining mechanism movably connected to said push rod when said push rod is driven towards said second position and configured to engage with said push rod to hold said plunger at said second position, said retaining mechanism including a plurality of grooves configured to engage with the at least one ratcheting tooth of the push rod, said plurality of grooves constructed and arranged to provide a defined dosage through said dispensing opening; and
  a collar having a recess for receiving said stop edge, said recess having a first edge and an opposed second edge,
wherein movement of said stop edge from a rest position adjacent said first edge of said collar to an actuating position closer to said opposed second edge of said collar compresses said elastic element against said opposed second edge of said collar and moves said push rod from said first position to said second position, said second position being closer to said dispensing opening than said first position, and
wherein said push rod is advanced in a linear and a non-rotatable direction to dispense a same defined dosage through said dispensing opening each time said drive mechanism drives said plunger.

2. The dispensing device according to claim 1, further comprising:
a dosage chamber configured to link a content of said container to said dispensing opening; and
a tip associated with said push button and configured to enter and exit said dosage chamber;
wherein said tip is configured to press out a product located in said dosage chamber by said dispensing opening.

3. A dispensing device, comprising:
a container;
a dispensing opening located at one end of said container;
a plunger located in said container;
a push button aligned with said push rod, said push button having a stop edge; and
a drive mechanism configured to move said push rod from a first position to a second position when said push button is pressed, and to hold said push rod at said second position, the drive mechanism including
  a push rod in contact with said plunger for moving said plunger linearly inside the container, the push rod including at least one ratcheting tooth;
  an elastic element positioned around said push rod;
  a retaining mechanism movably connected to said push rod when said push rod is driven towards said second position and configured to engage with said push rod to hold said plunger at said second position, said retaining mechanism including a plurality of grooves configured to engage with said at least one ratcheting tooth of the push rod; and a collar having a recess for receiving said stop edge, said recess having a first edge and an opposed second edge, wherein movement of said stop edge from a rest position adjacent said first edge of said collar to an actuating position closer to said opposed second edge of said collar compresses said elastic element against said opposed second edge of said collar and moves said push rod from said first position to said second position, wherein the movement of said push rod from said first position to said second position presses said push rod against the plunger to move the plunger closer to the dispensing opening, and wherein said push rod is advanced in a linear and a non-rotatable direction, and wherein a same defined dosage is dispensed through said dispensing opening each time said drive mechanism advances said push rod and causes at least one ratcheting tooth to engage one of said plurality of grooves.

4. A dispensing device, comprising:
a container;
a dispensing opening located at one end of said container;
a plunger located in said container;
a push button associated with said plunger, said push button having a stop edge; and
a drive mechanism configured to drive said plunger linearly inside said container from a first position towards said dispensing opening when said push button is pressed and to hold said plunger at a second position, the drive mechanism including
  a push rod in contact with said plunger for moving said plunger linearly inside the container, said push rod being aligned with the push button and including a plurality of grooves having a pitch configured to provide a defined dosage through the dispensing opening;
  an elastic element positioned around said push rod;
  a retaining mechanism movably connected to said push rod when said push rod is driven towards said second position and configured to engage with said push rod to hold said plunger at said second position, said retaining mechanism including ratcheting teeth configured to engage with said plurality of grooves of the push rod; and
  a collar having a recess for receiving said stop edge, said recess having a first edge and an opposed second edge, wherein movement of said stop edge from a rest position adjacent said first edge of said collar to an actuating position closer to said opposed second edge of said collar compresses said elastic element against said opposed second edge of said collar and moves said push rod from said first position to said second position, said second position being closer to said dispensing opening than said first position.

5. The dispensing device of claim 1, wherein said push button and said push rod are collinear.

6. The dispensing device of claim 5, wherein a central axis of said push button and a central axis of said push rod are aligned, said central axis of said push button extending along said central axis of said push rod.

7. The dispensing device of claim 3, wherein said at least one ratcheting tooth includes a ramped outer surface, said ramped outer surface sloping toward said dispensing opening.

8. The dispensing device according to claim 4, further comprising:
a dosage chamber configured to link a content of said container to said dispensing opening; and
a tip associated with said push button and configured to enter and exit said dosage chamber,
wherein said tip is configured to press out a product located in said dosage chamber by said dispensing opening.

9. The dispensing device according to claim 4, wherein the push button and push rod are collinear.

10. The dispensing device of claim 4, wherein a central axis of said push button and a central axis of said push rod are aligned, said central axis of said push button extending along said central axis of said push rod.

11. A dispensing device, comprising:
a container;
a dispensing opening located at one end of said container;
a plunger located in said container;
a push button associated with said plunger; and
a drive mechanism configured to drive said plunger linearly inside said container from a first position towards said dispensing opening when said push button is pressed and to hold said plunger at a second position, the drive mechanism including
  a push rod in contact with said plunger for moving said plunger linearly inside the container, said push rod including at least one ratcheting tooth; and
  a retaining mechanism movably connected to said push rod when said push rod is driven towards said second position and configured to engage with said push rod to hold said plunger at said second position, said retaining mechanism including a plurality of grooves configured to engage with the at least one ratcheting tooth of the push rod, said plurality of grooves constructed and arranged to provide a defined dosage through said dispensing opening, wherein said push button is collinear with the push rod,
wherein said second position is closer to said dispensing opening than said first position, and
wherein said push rod is advanced in a linear and a non-rotatable direction to dispense a same defined dosage through said dispensing opening each time said drive mechanism drives said plunger.

* * * * *